United States Patent [19]

Schuster

[11] Patent Number: 5,107,018

[45] Date of Patent: Apr. 21, 1992

[54] PROCESS FOR THE PREPARATION OF LOWER POLYHYDRIC ALCOHOLS

[75] Inventor: Ludwig Schuster, Limburgerhof, Fed. Rep. of Germany

[73] Assignee: BASF Aktiengesellschaft, Ludwigshafen, Fed. Rep. of Germany

[21] Appl. No.: 567,125

[22] Filed: Aug. 13, 1990

[30] Foreign Application Priority Data

Aug. 26, 1989 [DE] Fed. Rep. of Germany ....... 3928285

[51] Int. Cl.$^5$ ................. C07C 29/141; C07C 29/145; C07C 31/20; C07C 31/22
[52] U.S. Cl. ................................ 568/863; 502/324; 502/331
[58] Field of Search ........................................ 568/863

[56] References Cited

U.S. PATENT DOCUMENTS

| | | | |
|---|---|---|---|
| 1,990,245 | 2/1935 | Mueller et al. | 568/863 |
| 3,030,429 | 4/1962 | Conradin et al. | 568/863 |
| 4,496,780 | 1/1985 | Arena | 568/863 |
| 4,950,812 | 8/1990 | Jacobs et al. | 568/863 |
| 5,026,927 | 6/1991 | Andrews et al. | 568/863 |

OTHER PUBLICATIONS

Ind. Eng. Chem. Prod. Res. Dev. 9, 210–212 (1970).
Chem. Ber. 76, 641–656 (1943).
Chem. Ber. 71, 2712–2716 (1938).

*Primary Examiner*—J. E. Evans
*Attorney, Agent, or Firm*—Keil & Weinkauf

[57] ABSTRACT

A process for the preparation of lower polyhydric alcohols by catalytic hydrogenation of aqueous saccharose solutions at elevated temperature and pressure using a catalyst of which the catalytically active material essentially contains the metals cobalt, copper and manganese in the following concentrations, the total weight of said metals being standardized as 100%:
from 0 to 100% w/w of cobalt,
from 0 to 85% w/w of copper and
from 0 to 80% w/w of manganese,
this said metal content of said catalytically active material comprising either cobalt alone or at least two of said metals, which active material may also contain added inorganic poly acids and/or heteropoly acids, wherein from 0.01 to 5% w/w of one or more base-acting metal compounds of metals from the first and second main groups and from group IIIA of the Periodic Table are added to the saccharose solution to be hydrogenated.

8 Claims, No Drawings

PROCESS FOR THE PREPARATION OF LOWER POLYHYDRIC ALCOHOLS

The present invention relates to a process for the preparation of lower polyhydric alcohols by catalytic hydrogenation of aqueous saccharose solutions at elevated temperature and pressure using a catalyst of which the catalytically active material essentially contains the metals cobalt, copper and manganese in the following concentrations, the total weight of said metals being standardized as 100%:
from 0 to 100% w/w of cobalt,
from 0 to 85% w/w of copper and
from 0 to 80% w/w of manganese,
the said metal content of said catalytically active material comprising either cobalt alone or at least two of said metals, which active material may also contain added inorganic poly acids and/or heteropoly acids.

For many years now, there has been a desire to utilize saccharose for the preparation of polyols, since this cheap renewable raw material is available in large quantities.

Thus it is known, for example, to hydrogenate saccharose solutions in methanol/water mixtures by means of a $CuO\text{-}CeO_2\text{-}SiO_2$ catalyst [*Ind. Eng. Chem. Prod. Res. Dev.* 9, 210–212 (1970)]. The hydrogenation is carried out in the presence of calcium hydroxide in a concentration of 2%, by weight of the saccharose. The result is a mixture of products containing approx. 31% w/w of glycerol, 16% w/w of ethylene glycol, 18% w/w of 1,2-propylene glycol, 16% w/w of hexitols and 19% w/w of other products. According to its originators, this process is not economical, however.

Natta et al [*Chem. Ber.* 76, 641–656 (1943)] carry out the hydrogenation of saccharose in alcoholic solution by means of copper chromite/barium chromite catalysts. This produces a yield of up to 54% of propylene glycol and 14% of glycerol, based on the saccharose used. No statements are made on the hydrogenation of saccharose in aqueous solution using such a catalyst system.

According to Weidenhagen et al [*Chem. Ber.* 71, 2712–2716 (1938)], the formation of glycerol may be suppressed, in the hydrogenation of saccharose, in favor of 1,2-propylene glycol if a two-stage hydrogenation process is used. In this case the saccharose is first hydrogenated in neutral aqueous solution to acetol using a nickel/molybdenum catalyst, after which the acetol is isolated and subsequently hydrogenated to 1,2-propylene glycol in an aqueous solution basified with calcium hydroxide, the catalyst used being a nickel/chromium catalyst. The drawback of this process is that two stages are required to form the product.

It is an object of the present invention to provide an economic process for the hydrogenation of saccharose to diols, triols and/or tetrols. It should be workable in a single stage and should provide the possibility of altering the composition of the mixture of products resulting from the hydrogenation, simply by changing the reaction conditions, such that said mixture may contain, as desired, predominantly diols and triols or triols and tetrols or, in particular, as the main product, 1,2,5,6-hexanetetrol, which otherwise occurs only as by-product. To this end, a re-usable catalyst system should be found which shows long-term stability as regards its selective action.

Accordingly, we have found a process for the preparation of lower polyhydric alcohols by catalytic hydrogenation of aqueous saccharose solutions at elevated temperature and pressure using a catalyst of which the catalytically active material essentially contains the metals cobalt, copper and manganese in the following concentrations, the total weight of said metals being standardized as 100%:
from 0 to 100% w/w of cobalt,
from 0 to 85% w/w of copper and
from 0 to 80% w/w of manganese,
the said metal content of said catalytically active material comprising either cobalt alone or at least two of said metals, which active material may also contain added inorganic poly acids and/or heteropoly acids, wherein from 0.01 to 5% w/w of one or more base-acting metal compounds of metals from the first and second main groups and from group IIIA of the Periodic Table are added to the saccharose solution to be hydrogenated.

According to the above definition, the catalysts used in the process of the invention may contain all three of said catalytically active metal components or be prepared from only two of said metal components or, alternatively, comprise the metal component cobalt only. However, it is advantageous to use catalysts which contain all three components, those being preferred which contain at least 5% w/w of manganese, based on the total weight of the catalytically active metal components—calculated as metal. The compositions A to C below are given by way of example to illustrate suitable compositions for a number of catalysts well-suited for carrying out the present process:

A
5–90% w/w of cobalt
5–80% w/w of copper
5–75% w/w of manganese

B
0–5% w/w of cobalt
25–75% w/w of copper
20–75% w/w of manganese

C
75–95% w/w of cobalt
0–5% w/w of copper
5–20% w/w of manganese

The catalysts used in the process of the invention are generally prepared by concurrent precipitation of the said metals, for example in the form of their hydroxides, oxide-hydrates, base salts or carbonates, from a solution of their salts, preferably their nitrates, sulfates or acetates, by the addition of a base, advantageously an aqueous mineral base such as caustic soda solution, caustic potash solution, sodium carbonate solution and/or potassium carbonate solution, followed by isolation of the precipitate, drying and calcination thereof. Precipitation is preferably carried out by the two-stage method described in DE-A 2,321,101, in which the metal salt solution is first adjusted to a pH of at least 8 with an alkali metal carbonate solution at a temperature of, in general, from 40° to 70° C., after which further metal salt solution is added to this precipitation mixture until the pH reaches 6.8 to 7.5.

The resulting precipitate is separated by usual methods, e.g. filtration or centrifugation, and then washed, dried and calcined. Calcination is generally carried out at a temperature of from 400° to 550° C. Drying and calcination converts the chemically heterogeneous precipitate of the difficulty soluble metal compounds concerned into a conglomerate of the oxides, mixed oxides and mixed-valency oxides of said metals. Before use, the catalyst thus obtained is activated by reduction with hydrogen, during which process all or part of the metal compounds contained therein is reduced to the corresponding metals. In general, this reduction is carried out at elevated temperature, preferably from 200° to 600° C., in a stream of hydrogen. Alternatively, this catalyst activation can take place in situ, i.e. during the saccharose hydrogenation process.

Catalysts having particularly advantageous mechanical properties may be obtained by adding to the metal salt solution, prior to precipitation, inorganic acids capable of forming poly acids or heteropoly acids, for example sulfuric, boric, phosphoric, molybdic, vanadic and tungstic acids and/or their salts such as trisodium phosphate, sodium tetraborate, potassium dihydrogen phosphate, calcium hydrogen phosphate, magnesium hydrogen borate, aluminum phosphate, sodium molybdate, ammonium molybdate, ammonium vanadate and/or sodium tungstate, followed by precipitation and processing of the precipitate as described above.

Alternatively, the said additives may be incorporated by doping them into mixtures of the oxides of the catalytically active metal components or into the calcined and, possibly, ground catalyst composition. To this end, the said solids are mixed with aqueous solutions of salts of the above acids and the resulting mixture is treated with a mineral acid such as nitric acid or sulfuric acid. The catalyst composition thus modified may, if desired, be worked to shaped catalysts and/or dried, calcined and activated in the above manner. The amount of additive introduced into the catalyst in this manner and remaining therein may be from 0.1 to 15% w/w, based on the calcined catalyst prior to reduction. This treatment generally improves the mechanical handling properties of the catalyst. For example, a catalyst powder made in this way shows less tendency to form clumps.

Following calcination and prior to reduction, the catalysts are advantageously conditioned, i.e. brought into a form most suitable for use in the variously specialized production plants. For example, where it is desired to hydrogenate saccharose solutions continuously, it will be preferred to operate with fixed-bed reactors (packed bubble columns or trickle-bed reactors) in which the catalyst bed consists of shaped catalysts or supported catalysts, whereas in batchwise operations the use of a powdered catalyst suspended in aqueous medium will be preferred.

To prepare such suspension catalysts, the calcined catalyst composition will be pulverized advantageously prior to reduction, generally in the wet state and preferably to an average particle size of from 0.005 to 0.5 mm.

The powdered, activated suspension catalysts are generally used in a concentration of from 50 to 70 g/kg of 50% w/w aqueous saccharose solution. If the concentration of the saccharose solution used is higher or lower, the amount of catalyst added thereto will be modified accordingly.

Supported catalysts are generally prepared by precipitating the catalyst components by the above method of precipitation onto a supporting material which is inert under the conditions of the reaction and which may, if desired, be in the form of shaped supports. Examples of suitable supporting materials are aluminum oxides, silicon dioxide, zirconium dioxide, steatite and kaolin. In the present process, however, we prefer to use the catalyst in the form of solid catalyst, i.e. without the incorporation of a supporting component.

Using the catalysts described above, it is possible, according to the invention, to hydrogenate aqueous saccharose solutions to mixtures of diols, triols and tetrols.

The composition of the hydrogenation products obtained with said catalysts depends on a number of factors. For example, particularly high yields of ethylene glycol and 1,2-propylene glycol are obtained when hydrogenation is carried out at a temperature of from 230° to 280° C., whereas higher concentrations of glycerol and 1,2,5,6-hexanetetrol are found in the hydrogenation product following a reaction carried out at a temperature of from 180° to 230° C. At temperatures above 280° C. there is a rise in the content of monohydric alcohols in the hydrogenation product, and at temperatures below 180° C. there is an increase in the amount of hexitols present, e.g. mannitol or sorbitol.

Using the present catalysts, the saccharose hydrogenation is generally carried out under a hydrogen pressure of from 200 to 700 bar, preferably from 250 to 300 bar. At pressures below 200 bar there is increased formation of hexitols, and above 700 bar the hydrogenation of the saccharose becomes more and more complete and leads to the formation of monohydric alcohols and even hydrocarbons. Between hydrogen pressures of 200 and 700 bar, the composition of the hydrogenation product is substantially dependent on the pressure used.

In the process of the invention it is preferred to use saccharose solutions having a saccharose content of from 30 to 60% w/w. The hydrogenation of more weakly concentrated saccharose solutions may be successfully carried out as regards the composition of the hydrogenation product, but is less economical due to the reduced space-time yield. At saccharose concentrations above 70% w/w, a reduction in selectivity as regards the resulting hydrogenation product is observed.

Obviously, to achieve high selectivity, it is important to effect thorough mixing of the saccharose solution, suspended catalyst and hydrogen gas, as is achieved, for example, by the use of a turbine stirrer in an autoclave.

The extent of hydrogenation can be monitored from the consumption of hydrogen. When only a small amount of hydrogen is absorbed by the reaction mixture, the reaction can be stopped. This point is generally reached after a few hours.

When the hydrogenation is to be carried out batchwise, the advantageously finely ground catalyst is generally placed in an autoclave in the form of a suspension in water. To aid suspension of the catalyst particles it may be advantageous to add to the aqueous suspension from 30 to 80% v/v of the polyols to be subsequently produced in the saccharose hydrogenation. Although the addition of other polyols is possible, this would hamper isolation of the individual hydrogenation products when working up the reaction mixture.

Using the above catalysts, saccharose is generally hydrogenated rapidly and thoroughly, with good selectivity, to the desired polyhydric alcohols. The repeated use of these catalysts shows, however, that although their activity remains unchanged, their selective action on the formation of industrially interesting diols, triols and tetrols decreases from one hydrogenation to the next, so that the catalyst becomes useless after about 5 to 6 hydrogenations (cycles) due to the insufficient selectivity. This drop in selectivity is particularly manifest from the formation of numerous byproducts.

We have now found that this loss of selectivity can be prevented, according to the invention, by adding base-acting compounds to the reaction medium. As a result, the catalyst can be re-used any desired number of times.

Examples of suitable base-acting compounds for use in the process of the invention are alkali metal hydroxides, alkaline earth metal hydroxides, alkali metal carbonates, alkaline earth metal carbonates, nitrogen bases such as tetraalkylammonium hydroxides or carbonates or compounds which convert to base-acting compounds under the conditions of the reaction. We prefer to use the hydroxides and carbonates of alkali metals and alkaline earth metals or mixtures thereof. A particularly beneficial effect on the ability of the catalyst to maintain its selective action is achieved by the addition of less readily soluble hydroxides and carbonates of metals in the first two main groups and in group IIIA of the Periodic Table. We particularly prefer to add lithium hydroxide and/or magnesium hydroxide to the reaction medium. Very good results, as regards maintaining constant selectivity, are obtained, for example, by the addition of calcium oxide or sodium carbonate. The addition of mixtures of base-acting compounds to the reaction medium may cause the individual compounds to influence each other synergistically with respect to their activity. For example, the addition of potassium oxide together with magnesium oxide has a synergistic effect.

The base-acting compounds are generally added to the saccharose solution to be hydrogenated in a concentration of from 0.01 to 5% w/w, preferably from 0.1 to 1% w/w, and advantageously in finely divided form or as a solution. Greater additions of such base-acting compounds do not impair the results of the saccharose hydrogenation, but they generally complicate the removal thereof, for which reason it is not advantageous to add greater amounts of said compounds.

By using the catalysts described above and adding base-acting compounds as proposed by the invention it is possible, by varying the conditions of reaction in the manner described above, to obtain mixture of hydrogenation products containing, as the main product, diols or mixtures of triols and tetrols, in an economical manner.

The diols-ethylene glycol and 1,2-propylene glycol- are used, for example, as components of antifreeze compositions, whereas 1,2,5,6-hexanetetrol is used together with glycerol as a cross-linking alcohol component in the manufacture of polyurethane foams.

EXAMPLES

EXAMPLE 1

In an autoclave equipped with a stirrer for mixing gases and liquids there were placed 42 g of activated catalyst (average particle size 0.1 mm) suspended in a solution of 24 g of ethylene glycol and 56 g of 1,2-propylene glycol in 120 g of water.

The catalyst used was one having the following formal composition prior to activation with hydrogen at 450° C.:
66.8% w/w of cobalt, calculated as CoO,
19.2% w/w of copper, calculated as CuO,
7.1% w/w of manganese, calculated as $Mn_3O_4$,
3.4% w/w of phosphate, calculated as $H_3PO_4$,
3.5% w/w of molybdenum, calculated as $MoO_3$.

This formaly corresponds to cobalt, copper and manganese contents of 72%, 21% and 7% w/w respectively, based on the total content of these three metals in the catalyst—standardized as 100% w/w.

Hydrogen was then pumped into the autoclave to produce an internal pressure of 160 bar, which increased to 280 bar as the reaction mixture was heated to the reaction temperature of 260° C. At this temperature, 400 g of a 50% w/w aqueous saccharose solution was pumped into the autoclave over a period of 1 hour. The internal pressure remained approximately constant, because the rise in pressure due to increase in volume was offset by hydrogen consumption. On completion of the saccharose feed, the pressure was adjusted to 300 bar by pumping in further hydrogen and kept at this level throughout hydrogenation.

After 3 hours, the hydrogenation was stopped by cooling the reaction mixture and letting the internal pressure down to 5 to 10 bar. The catalyst was allowed to settle, and the liquid reaction mixture was removed from the autoclave through a vertical tube such that the catalyst remained in the autoclave.

The discharged reaction mixture thus obtained contained 60% w/w of water and 40% w/w of organic components. Analysis of the latter by high-pressure liquid chromatography gave the following results:
65.5% w/w of 1,2-propylene glycol,
19.5% w/w of ethylene glycol,
4.9% w/w of 1,2-butylene glycol,
3.6% w/w of hexane-1,2,5,6-tetrol,
0.8% w/w of hexane 1,2,6-triol,
3.0% w/w of monohydric alcohols such as ethanol, n-propanol, 2-butanol,
2.7% w/w of unidentified compounds.

Hydrogenation was carried out in the same manner a number of times using the same catalyst, in order to determine the useful life of the catalyst expressed as catalyst cycles. It was found that when only pure saccharose solution was used, the propylene glycol content of the effluent decreased linearly with increase in the number of cycles.

Following the sixth hydrogenation, the effluent contained 62.3% w/w of water and 37.7% w/w of organic components of the following composition
30.7% w/w of 1,2-propylene glycol,
10.7% w/w of ethylene glycol,
9.9% w/w of 1,2-butylene glycol,
13.8% w/w of hexane-1,2,5,6-tetrol, 11.2% w/w of hexane 1,2,6-triol,
5.5% w/w of monohydric alcohols,
18.2% w/w of unidentified compounds.

EXAMPLE 2

Hydrogenation was carried out as in Example 1 except that 1 g of finely divided lithium hydroxide was suspended in the 400 g of saccharose solution to be hydrogenated. After 18 catalyst cycles, the effluent still contained 90% of the content of 1,2-propylene glycol found in the effluent following the first hydrogenation.

EXAMPLE 3

Hydrogenation was carried out as described in Example 1. 1 g of finely divided magnesium hydroxide, used as base-acting compound, was suspended in the 400 g of aqueous saccharose solution. Following 9 cycles, the content of 1,2-propylene glycol in the effluent was still 95% of that obtained after the first hydrogenation.

EXAMPLE 4

Hydrogenation was carried out as described in Example 1, except that 2 g of finely divided calcium oxide were suspended in the 400 g of saccharose solution. Following 19 cycles, the content of 1,2-propylene glycol in the effluent was still 91% of that obtained after the first hydrogenation.

EXAMPLE 5

Hydrogenation was carried out as described in Example 1, except that the 400 g of aqueous saccharose solution contained, finely suspended therein 1 g of magnesium oxide containing 4% w/w of potassium oxide. Following 36 cycles, the content of 1,2-propylene glycol in the effluent was still 89% of that obtained after the first hydrogenation.

EXAMPLE 6

In an autoclave having a capacity of 10 liters, 370 g of activated catalyst (average particle size 0.1 mm) and 20 g of magnesium oxide containing 2% w/w of potassium oxide were suspended in 5,700 g of a 50% w/w aqueous saccharose solution. The catalyst used had the same chemical composition as that used in Example 1.

Hydrogen was then pumped into the autoclave to create an internal pressure of 180 bar, after which the reaction mixture was heated to 215° C. with vigorous mixing over 2 hours. A sharp rise in hydrogen consumption at 180° C. indicated the commencement of the reaction. Fresh hydrogen was continuously pumped in to compensate for the pressure drop caused by hydrogen consumption, by which means the pressure in the autoclave was maintained between 280 and 300 bar.

After 4.5 hours, hydrogenation was stopped by cooling and depressurizing the autoclave. The liquid effluent was separated from the catalyst as described in Example 1, and hydrogenation was repeated in the above manner a number of times. It was found that the catalyst could be used any desired number of times under the reaction conditions stated without any loss of activity.

The effluent obtained in this manner contained 55% w/w of water and 45% w/w of organic components of the following composition:

30.0% w/w of hexane-1,2,5,6-tetrol,
18.0% w/w of glycerol,
23.3% w/w of 1,2-propylene glycol,
11.2% w/w of ethylene glycol,
3.0% w/w of butylene glycol,
7.0% w/w of hexane 1,2,6-triol,
0.5% w/w of monohydric alcohols,
7.0% w/w of unidentified compounds.

To isolate the organic components from the effluent, the water was first removed by evaporation under reduced pressure. The residue was then subjected to fractional distillation under reduced pressure to give ethylene glycol, propylene glycol, glycerol and butylene glycol. The remaining viscous residue was then purified by high-vacuum distillation in a thin-layer evaporator.

We claim:

1. A process for the preparation of lower polyhydric alcohols from aqueous saccharose solutions which comprises: adding from 0.01 to 5% w/w of one or more base-acting metal compounds of metals from the first and second main groups and from group IIIA of the Periodic Table to the aqueous saccarose solution and hydrogenating the aqueous saccarose solution at an elevated temperature and an elevated pressure in the presence of a catalyst, said catalyst containing as its active material one or more of the metals cobalt, copper and manganese in the following concentrations, the total weight of said metals being standardized as 100%:
from 0 to 100% w/w of cobalt,
from 0 to 85% w/w of copper and
from 0 to 80% w/w of manganese,
with the proviso that the catalyst contains (a) all three of the metals, (b) any two of the metals, or (c) only cobalt among the three metals.

2. A process as defined in claim 1, wherein from 0.1 to 1% w/w of one or more base-acting metal compounds of metals from the first and second main groups and from group IIIA of the Periodic Table are added to the saccharose solution to be hydrogenated.

3. A process as defined in claim 1, wherein the base-acting compounds used are basic alkali metal and/or alkaline earth metal compounds.

4. A process as defined in claim 1, wherein the base-acting compounds used are the hydroxides, oxides and/or carbonates of lithium, sodium, potassium, magnesium and/or calcium.

5. A process as defined in claim 1, wherein the hydrogenation is carried out at a temperature of from 230° to 280° C.

6. A process as defined in claim 1, wherein the hydrogenation is carried out at a temperature of from 180° to 230° C.

7. The process of claim 1, wherein the active material of the catalyst also includes inorganic poly acids and/or heteropoly acids.

8. The process of claim 1, wherein the active material of the catalyst includes at least 5% w/w of manganese.

* * * * *